(12) United States Patent
Abe et al.

(10) Patent No.: US 7,450,982 B2
(45) Date of Patent: Nov. 11, 2008

(54) MAGNETIC RESONANCE IMAGING SYSTEM AND METHOD

(75) Inventors: Takayuki Abe, Chiba (JP); Tetsuhiko Takahashi, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 269 days.

(21) Appl. No.: 10/549,340

(22) PCT Filed: Mar. 12, 2004

(86) PCT No.: PCT/JP2004/003274

§ 371 (c)(1),
(2), (4) Date: Sep. 13, 2005

(87) PCT Pub. No.: WO2004/080302

PCT Pub. Date: Sep. 23, 2004

(65) Prior Publication Data

US 2006/0183996 A1     Aug. 17, 2006

(30) Foreign Application Priority Data

Mar. 14, 2003   (JP) ............................. 2003-069530

(51) Int. Cl.
*A61B 5/055* (2006.01)
(52) U.S. Cl. .................... 600/410; 600/420; 324/309
(58) Field of Classification Search ................ 600/420, 600/410; 324/307, 309
See application file for complete search history.

(56) References Cited

U.S. PATENT DOCUMENTS

| | | | | |
|---|---|---|---|---|
| 4,678,996 A * | 7/1987 | Haacke et al. | ................ | 324/309 |
| 4,740,749 A * | 4/1988 | Yamamoto et al. | ........... | 324/309 |
| 4,748,410 A * | 5/1988 | Macovski | ................... | 324/309 |
| 4,885,537 A * | 12/1989 | Suzuki | ........................ | 324/309 |
| 5,311,132 A * | 5/1994 | Noll et al. | .................... | 324/309 |
| 5,348,011 A * | 9/1994 | NessAiver | ................... | 600/411 |
| 5,590,654 A * | 1/1997 | Prince | ......................... | 600/420 |
| 5,713,358 A * | 2/1998 | Mistretta et al. | ............. | 600/420 |
| 5,830,143 A * | 11/1998 | Mistretta et al. | ............. | 600/420 |
| 5,897,496 A * | 4/1999 | Watanabe | .................... | 600/413 |
| 5,977,769 A * | 11/1999 | Bornert et al. | ............... | 324/306 |
| 5,987,348 A * | 11/1999 | Fischer et al. | ................ | 600/413 |
| 5,997,883 A * | 12/1999 | Epstein et al. | ............... | 324/306 |
| 6,068,595 A * | 5/2000 | Miyazaki et al. | ............. | 600/410 |
| 6,121,775 A * | 9/2000 | Pearlman | ..................... | 324/309 |
| 6,195,579 B1 * | 2/2001 | Carroll et al. | ................ | 600/420 |
| 6,198,959 B1 * | 3/2001 | Wang | ........................... | 600/413 |
| 6,377,835 B1 * | 4/2002 | Schoenberg et al. | ......... | 600/419 |

(Continued)

FOREIGN PATENT DOCUMENTS

JP          10-5191          1/1998

(Continued)

*Primary Examiner*—Ruth S. Smith
*Assistant Examiner*—Jonathan G Cwern
(74) *Attorney, Agent, or Firm*—Cooper & Dunham LLP

(57) ABSTRACT

A magnetic resonance imaging system is provided wherein measurement data (k space data) is extracted easily (and instantaneously) after imaging a plurality of times phases, and an image can be displayed in dynamic MRA measurement employing a contrast medium. Dynamic measurement is carried out, including extracting the time phase evaluation values (e.g. the origin data in k space) in respective time phases and then automatically extracting a data set including a time phase where the time phase evaluation value reaches a specified threshold value.

22 Claims, 9 Drawing Sheets

U.S. PATENT DOCUMENTS

| | | | |
|---|---|---|---|
| 6,380,740 B1 * | 4/2002 | Laub | 324/309 |
| 6,381,486 B1 * | 4/2002 | Mistretta et al. | 600/420 |
| 6,556,856 B1 * | 4/2003 | Mistretta et al. | 600/420 |
| 6,580,937 B2 * | 6/2003 | Ho et al. | 600/415 |
| 6,597,937 B2 * | 7/2003 | Liu et al. | 600/420 |
| 6,603,992 B1 * | 8/2003 | Debbins et al. | 600/420 |
| 6,611,144 B2 * | 8/2003 | Abe | 324/309 |
| 6,630,828 B1 * | 10/2003 | Mistretta et al. | 324/309 |
| 6,639,211 B1 * | 10/2003 | Anand et al. | 250/282 |
| 6,643,534 B2 * | 11/2003 | Foo et al. | 600/420 |
| 6,653,834 B2 * | 11/2003 | Beck et al. | 324/309 |
| 6,683,454 B2 * | 1/2004 | Rehwald et al. | 324/307 |
| 6,745,064 B2 * | 6/2004 | Fuderer et al. | 600/410 |
| 6,784,664 B2 * | 8/2004 | Liang et al. | 324/309 |
| 6,801,800 B2 * | 10/2004 | Miyazaki et al. | 600/410 |
| 6,914,429 B2 * | 7/2005 | Ookawa | 324/309 |
| 7,167,740 B2 * | 1/2007 | Abe et al. | 600/420 |
| 2002/0032376 A1 * | 3/2002 | Miyazaki et al. | 600/410 |
| 2002/0087068 A1 * | 7/2002 | Foo | 600/413 |
| 2002/0087069 A1 * | 7/2002 | Ho et al. | 600/415 |
| 2002/0107438 A1 * | 8/2002 | Liu et al. | 600/410 |
| 2003/0011368 A1 * | 1/2003 | Abe | 324/309 |
| 2003/0032877 A1 * | 2/2003 | Watts et al. | 600/410 |
| 2003/0060698 A1 * | 3/2003 | Mistretta | 600/410 |
| 2003/0071618 A1 * | 4/2003 | DiCarlo | 324/307 |
| 2003/0080737 A1 * | 5/2003 | Loeffler | 324/307 |
| 2003/0135103 A1 * | 7/2003 | Mistretta | 600/410 |
| 2004/0027124 A1 * | 2/2004 | Abe et al. | 324/309 |
| 2004/0061496 A1 * | 4/2004 | Ookawa | 324/307 |
| 2005/0033159 A1 * | 2/2005 | Mistretta et al. | 600/420 |
| 2005/0058352 A1 * | 3/2005 | Deliwala | 382/232 |
| 2005/0203377 A1 * | 9/2005 | Watts et al. | 600/410 |
| 2006/0183996 A1 * | 8/2006 | Abe et al. | 600/410 |
| 2006/0232273 A1 * | 10/2006 | Takizawa et al. | 324/309 |

FOREIGN PATENT DOCUMENTS

| | | |
|---|---|---|
| JP | 2000-350715 | 12/2000 |
| JP | 2002-165775 | 6/2002 |

* cited by examiner

MAGNETIC RESONANCE IMAGING SYSTEM AND METHOD

TECHNICAL FIELD

This invention relates to a magnetic resonance imaging (hereinafter called "MRI") apparatus for acquiring a tomogram of a desired portion of a subject by utilizing a nuclear magnetic resonance (hereinafter called "NMR") phenomenon. More particularly, the invention relates to an MRI apparatus capable of easily depicting an artery phase image of bloodstream motion containing a contrast agent when the blood vessel system is depicted by using a T1 shortening type contrast agent such as Gd-DTPA.

BACKGROUND ART

A magnetic resonance imaging apparatus measures a density distribution of an atomic nucleus spin (hereinafter merely called "spin"), a relaxation time distribution, etc, at a desired inspection portion in a subject by utilizing the NMR phenomenon and displays an image of an arbitrary section of the subject from the measurement data. Particularly, the magnetic resonance imaging apparatus has an imaging function called "contrast enhanced MR angiography" (hereinafter abbreviated as "CE-MRA") that depicts the blood vessel with high signals by using a contrast agent.

When a contrast agent is injected from an elbow vein, for example, the contrast agent ejected through the heart first enhances the signals of the artery system and then the vein system through the capillary. In clinical diagnosis of diseases, depiction of not only the artery system but also the vein system is necessary in some cases, and imaging by CE-MRA is preferably carried out in some cases continuously throughout a plurality of time phases. Such an imaging method is called "dynamic MRA measurement (hereinafter abbreviated as "dynamic measurement").

In this dynamic measurement, time resolution is of importance to improve diagnostic accuracy of the diseases but it has a trade-off relation with spatial resolution or a signal to noise ratio (S/N) determined by a phase encode number and a slice encode number. Therefore, a method that divides the measurement space (hereinafter abbreviated as "k space") into a plurality of areas, shares measurement data of the same area among a plurality of time phases and substantially shortens the imaging time per measurement is disclosed in JP-A-2002-177240.

In dynamic measurement, however, the number of measurement data (number of time phases) becomes great. In the case of three-dimensional imaging, in particular, the operation of extracting only three-dimensional data constituting an artery phase (time phase in which the artery is mainly depicted) necessary for the diagnosis from among a large number of measurement data is complicated and there remains the problem that generating and review (diagnosis) of the two-dimensional image of the artery phase cannot be made immediately after imaging.

JP-A-2002-177240 described above does not disclose a method for extracting the measurement data of a desired artery phase from among a plurality of time series data measured.

DISCLOSURE OF THE INVENTION

In an aspect Of this disclosure, an MRI apparatus is provided that, in dynamic measurement, can extract easily (or instantaneously) an intended time phase (artery phase, for example) after imaging and can create a two-dimensional projection image in that artery phase.

To accomplish this object, the invention employs the following construction.

In other words, in an MRI apparatus including measurement control means for dividing a k space into a high frequency measurement area containing an origin of the k space and measured at a high frequency and a plurality of low frequency measurement areas not containing the origin and measured at a low frequency, and repeating measurement of the high frequency measurement area and measurement of each of the low frequency measurement areas between the measurements to obtain k space data; signal processing means for conducting image reconstruction by using the k space data; and display means for displaying the resulting image; the signal processing means acquires a time phase evaluation value from the high frequency measurement area, determines a time phase in which the time phase evaluation value reaches at least a predetermined threshold value, selects the high frequency measurement area containing the time phase and at least one low frequency measurement area measured time-wise close to the high frequency measurement area as an image reconstruction set and executes image reconstruction by using the k space data of the set.

Consequently, the timing at which a desired time phase of the subject starts can be easily acquired in dynamic measurement. As a result, an image reflecting the desired time phase can be acquired easily and instantaneously. Particularly in contrast agent MRA, the k space data of the intended artery phase can be easily and instantaneously extracted from a large number of time series measurement data containing a plurality of time phases and the image can be displayed.

According to a preferred embodiment, at least one of the low frequency measurement areas constituting the image reconstruction set is a measurement area measured immediately before or immediately after the high frequency measurement area constituting the image reconstruction set. Further, selection of each measurement area constituting the image reconstruction set is made in such a fashion as to contain the whole area of the k space.

Consequently, the image on which the desired time phase is more reflected can be acquired by using the k space data of the high frequency measurement area having contrast information of a desired time phase and the low frequency measurement areas time-wise close to the high frequency measurement area. In contrast agent MRA, in particular, since the concentration of the contrast agent changes time-wise, the image in which the contrast of the artery phase is more strongly reflected can be acquired as the concentration of the contrast medium becomes high and the blood vessel is depicted at high signals.

According to a preferred embodiment, the measurement control means controls the measurement sequence of each measurement area in such a fashion that the measurement period of the high frequency measurement area contains the time phase described above. More concretely, the signal processing means predicts the timing of the time phase from the time change of the time phase valuation values and the measurement control means controls the measurement sequence of each measurement area on the basis of the predicted timing.

According to the means described above, the measurement sequence of each measurement area can be controlled (changed) while following up the time change of the time phase evaluation values and the measurement period of the high frequency measurement area is allowed to reliably contain the desired time phase. As a result, the image more strongly reflecting the desired time phase can be acquired. Particularly in contrast medium MRA, the image reflecting the contrast of the artery phase can be reliably acquired.

According to another preferred embodiment, the signal processing means described above determines the time phase described above after repetition measurement described above.

According to the means described above, the start timing of the desired time phase can be acquired reliably and easily after the dynamic measurement, too, and the image reflecting that time phase can be easily acquired.

According to another preferred embodiment, the time phase evaluation value is a substantial peak value of the k space data in the high frequency measurement area. Alternatively, the time phase evaluation value is an addition value after uni-dimensional data in the read direction containing the k space origin in the high frequency measurement area is subjected to Fourier transform.

According to the means described above, the signal value having a high S/N more satisfactorily reflecting the time phase of the subject is used as the time phase evaluation value, so that the time phase of the subject can be recognized more reliably and easily.

According to another preferred embodiment, the threshold value described above is at least 1.8 times a base line value of the time phase evaluation value. Alternatively, the threshold value is at least 80% of a maximum value of the time phase evaluation values.

According to these means, the k space data of the intended artery phase can be extracted easily and instantaneously from among a large number of time series measurement data containing a plurality of time phases built up during the dynamic measurement in contrast agent MRA, in particular, and the image can be displayed.

According to another preferred embodiment, the display means displays the time phase evaluation values in a time series. A signal intensity change curve approximately representing the time change of the time phase evaluation values displayed in the time series by connecting them with one another is displayed. The apparatus further includes means for designating the threshold value or means for designating the time phase. The signal processing means described above selects the high frequency measurement area closest to the time phase designated. The apparatus further includes means for displaying the measurement sequence of each measurement area and the measurement period by using the same time axis as that of the time phase evaluation values, capable of selecting this display as an image reconstruction set. In this instance, display of each measurement area selected is made different from display of other measurement areas not selected.

According to the means described above, the condition (time phase) of the subject can be easily recognized through the time change of the time phase evaluation value. Setting and change of the threshold value, designation and change of the start timing of the desired time phase and direct designation of the measurement area set for image reconstruction can be easily made on the display screen and the image reflecting them can be easily acquired. In contrast agent MRA, in particular, fine adjustment of the start timing of the artery phase or direct designation of the measurement area set for image reconstruction is particularly useful for the diagnosis in the sense that the image reflecting more reliably the condition of the artery phase is acquired.

According to another preferred embodiment, the k space data described above is data reflecting the concentration information of the contrast agent injected into the subject, the image contains the blood vessel image of the subject and the time phase is the one in which artery is emphasized by the contrast agent. Consequently, in dynamic MRA using the contrast agent, the image reliably catching the artery phase of the blood vessel can be easily acquired.

According to another preferred embodiment, the k space described above is a three-dimensional space that comprises a slice encode direction, a phase encode direction and a read direction and division of the k space is division by a plane parallel to the read direction. In this case, the image processing described above executes a projection processing on a two-dimensional plane after three-dimensional reconstruction. Alternatively, the k space is a two-dimensional space that comprises the read direction and the phase encode direction and division of the k space is division by a line parallel to the read direction.

In the two- or three-dimensional dynamic measurement using the contrast medium, too, the image reliably catching the desired time phase can be acquired easily and instantaneously. In contrast medium MRA, in particular, the two- or three-dimensional blood vessel image can be easily acquired.

BRIEF DESCRIPTION OF THE DRAWINGS

FIG. 1a is a view showing the case where the three-dimensional k space is divided by a plane Kx-Kz defined by a read direction (Kx) and a slice encode direction (Kz) into a high frequency measurement area B containing an origin and other low frequency measurement areas A and C in terms of Kx=0 plane.

FIG. 1b is a view showing the case where the three-dimensional k space is divided by a plane Kx-Ky defined by the read direction (Kx) and a phase encode direction (Ky) into the high frequency measurement area B containing the origin and other low frequency measurement areas A and C in terms of Kx=0 plane.

FIG. 2(a) is a view showing an example of the case where each measurement area is measured in a predetermined measurement sequence.

FIG. 2(b) is a view showing an example where the measurement sequence of each measurement area is changed in such a fashion as to cope with the change of a time phase evaluation value.

FIG. 2(c) is a view showing another example where the measurement sequence of each measurement area is changed in such a fashion as to cope with the change of the time phase evaluation value.

FIG. 3a is a view showing a plot of time phase evaluation values acquired in the measurement sequence of each measurement area shown in FIG. 2(b) and a graph of its signal intensity change curve, and a measurement sequence of each measurement area and its measurement period by commonly using the same time axis as that of the graph.

FIG. 3b is a view showing, for the example of FIG. 3a, a projection image of a selected artery phase and a mode of area division of the k space are combined and displayed on one screen.

FIG. 5a is a view showing a graph representing the mode of time change by plotting the time phase evaluation values and a display example of the measurement sequence of each divided measurement area.

FIG. 5b is a view showing, for the example of FIG. 5a, a projection image of a selected artery phase and a mode of area division of the k space are combined and displayed on one screen.

BEST MODE FOR CARRYING OUT THE INVENTION

Modes for carrying out the invention will be hereinafter explained in detail with reference to the accompanying drawings.

First, an overall construction of an MRI apparatus to which the invention is applied will be explained with reference to a block view of FIG. 8.

Figure 8:
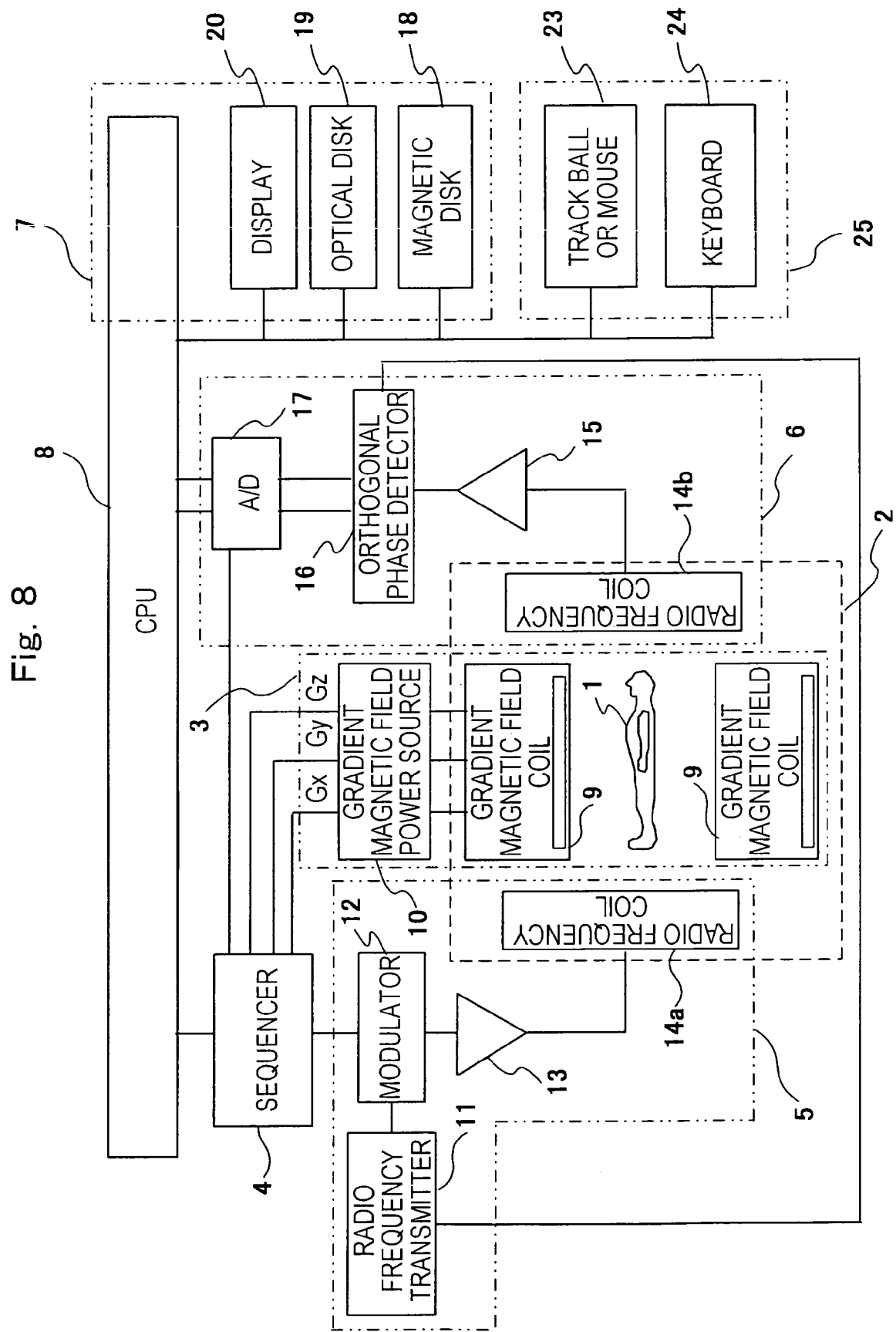
FIG. 8 is a block view showing overall constructions of nuclear magnetic imaging apparatuses according to the invention and the prior art.

The MRI apparatus shown in FIG. 8 acquires a tomogram of a subject by utilizing a nuclear magnetic resonance (NMR) phenomenon and includes a static magnetic field generation system 2, a magnetic field gradient generation system 3, a transmission system 5, a reception system 6, a signal processing system 7, a sequencer 4, a central processing unit (CPU) 8 and an operation portion 25 as shown in FIG. 8.

The static magnetic field generation system 2 generates a uniform static magnetic field around the subject 1 in a body axis direction or a direction intersecting at right angles the body axis. Magnetic field generation means of a permanent magnet system, or a normal conduction system or a super-conduction system is arranged inside a space having a certain expansion around the subject 1.

The magnetic field gradient generation system 3 has gradient magnetic field coils 9 wound in three axial directions of X, Y and Z and a gradient magnetic field power source 10 for driving the respective gradient magnetic field coils. The gradient magnetic fields Gx, Gy and Gz of the three axial directions of X, Y and Z are applied to the subject 1 when the gradient magnetic field power source 10 of each coil is driven in accordance with the instruction of the sequencer 4 to be later described. A slice plane can be set to the subject 1 depending on the mode of application of the gradient magnetic fields.

The sequencer 4 repeatedly applies radio frequency magnetic field pulses in a certain pulse sequence for generating the nuclear magnetic resonance to the atomic nuclei constituting the living body tissue of the subject 1, operates under control of the CPU 8 and transmits various instructions necessary for collecting data of the tomogram of the subject 1 to the transmission system 5, the magnetic field gradient generation system 3 and the reception system 6.

The transmiddion ststem 5 irradiates the radio frequency magnetic field to generate the nuclear magnetic resonance in the atomic nuclei of the atoms constituting the living body tissue of the subject 1, and includes a radio frequency oscillator 11, a modulator 12, a radio frequency amplifier 13 and radio frequency coil 14a on the transmission side. The radio frequency pulses outputted from the radio frequency oscillator 11 are amplitude-modulated by the modulator 12 in accordance with the instruction of the sequencer 4 and after being amplified by the radio frequency amplifier 13, the radio frequency pulses so amplitude-modulated are supplied to the radio frequency coil 14a arranged in the proximaty of the subject 1 so that the electromagnetic waves can be irradiated to the subject 1.

The reception system 6 is for detecting the echo signal (NMR signal) emitted owing to the nuclear magnetic resonance of the atomic nuclei in the living body tissue of the subject 1 and includes a radio frequency coil 14b on the reception side, an amplifier 15, an orthogonal phase detector 16 and an A/D converter 17. The response electromagnetic wave (NMR signal) of the subject 1 due to the electromagnetic waves irradiated from the radio frequency coil 14a on the transmission side is detected by the radio frequency coil 14b arranged in the proximity of the subject 1, is amplified by the amplifier 15 and is then divided into two systems of signals orthogonal to each other by the orthogonal phase detector 16 at the timing instructed from the sequencer 4. Each signal is converted to a digital quantity by the A/D converter 17 and is sent to the signal processing system 7.

The signal processing system 7 executes various data processing and display and preservation of the processing result and includes an external storage device such as an optical disk 19, a magnetic disk 18, etc, and a display 20 such as CRT. When the data is inputted from the reception system 6 to the CPU 8, the CPU 8 executes processing such as signal processing and image reconstruction, displays the tomogram of the subject 1 as the result on the display 20 and records it to the magnetic disk 18, etc, of the external storage device.

The operation portion 25 is for inputting various control information of the MRI apparatus and control information of the processing executed by the signal processing system 7 and includes a track ball or mouse 23 and a keyboard 24. This operation portion 25 is arranged close to the display 20 and the operator interactively controls various processing of the MRI apparatus through the operation portion 25 while watching the display 20.

Incidentally, in FIG. 8, the radio frequency coils 14a and 14b on the transmission and reception sides and the gradient magnetic field coil 9 are arranged inside the magnetic field space of the static magnetic field generation system 2 arranged in the space surrounding the subject 1.

Next, the MRI apparatus of the invention includes a pulse sequence for conducting dynamic measurement, more concretely a gradient echo type pulse sequence having a short repetition time, as the pulse sequence. The pulse sequence is stored as a program in the magnetic disk 18, for example, and is read into and executed by the CPU 8, whenever necessary. The pulse sequence for conducting dynamic measurement will be hereinafter explained in detail.

Figure 9:
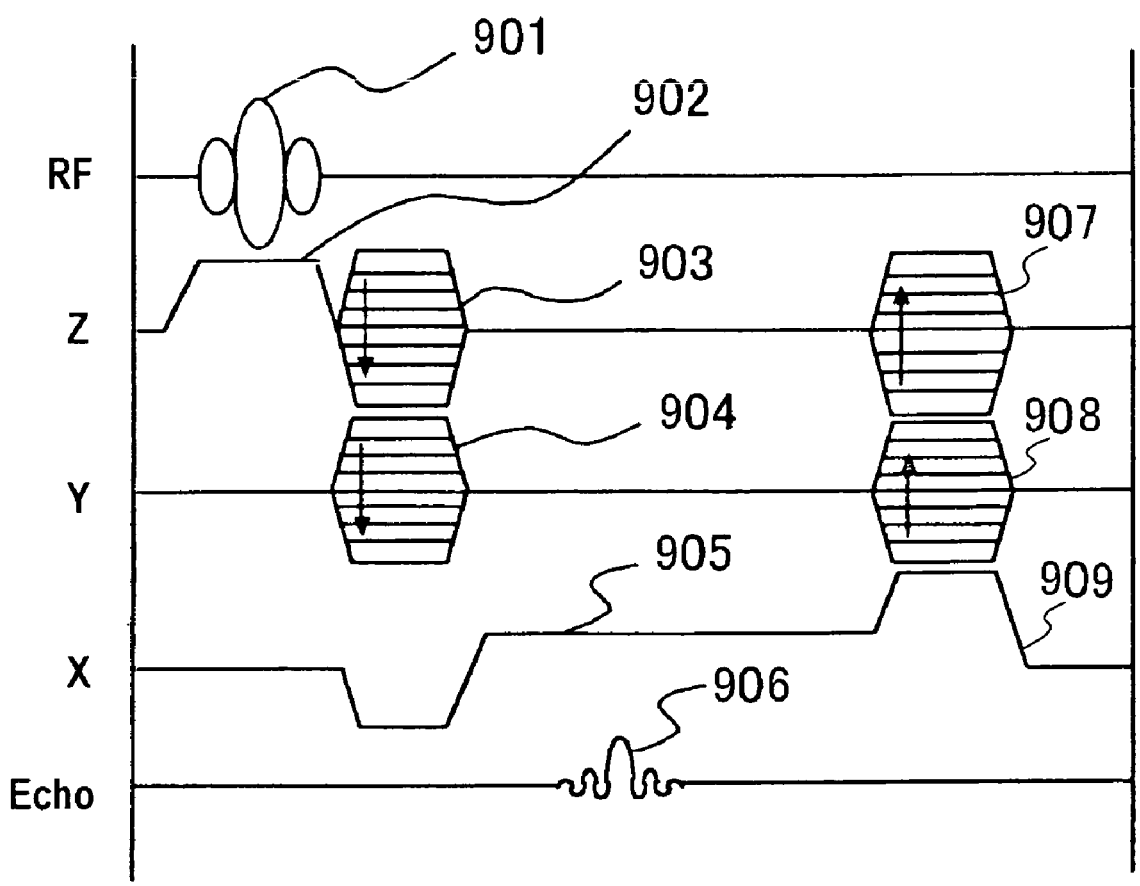
FIG. 9 is a pulse sequence view of a three-dimensional gradient echo system used in the invention.

FIG. 9 shows an example of the pulse sequence used for three-dimensional dynamic measurement that is a known gradient echo system pulse sequence. In FIG. 9, X, Y and Z directions are a read direction, a phase encode direction and a slice direction, respectively. An imaging area inclusive of an object blood vessel is excited by applying a gradient magnetic field 902 for selecting the imaging area simultaneously with the irradiation of an RF pulse 901. Next, a slice encode gradient magnetic field 903 and a phase encode gradient magnetic field 904 are applied and a readout gradient magnetic field 905 is further applied to measure an echo signal 906. After the echo signal 906 is measured, rewind gradient magnetic fields 907 and 908 are applied so as to return the application quantity of the slice encode gradient magnetic field 903 and the phase encode gradient magnetic field 904 to zero. A spoiler gradient magnetic field 909 is applied to greatly disperse the phase of transverse magnetization and to distinguish it.

The process from RF pulse irradiation 901 to next irradiation of the RF pulse is repeated in a short TR such as a repetition time of several ms to dozens of ms. In three-dimensional measurement, echo signals having different slice encode or phase encode are measured for each TR. In two-dimensional measurement, echo signals having only different phase encode are measured without applying the slice encode. When the slice encode number is Ns and the phase encode number of Np, three-dimensional data of a three-dimensional area (three-dimensional volume area or slab area) inclusive of the object blood vessel is generally acquired by repetition of Ns×Np. In two-dimensional measurement, two-dimensional data of a two-dimensional area inclusive of the object blood vessel is generally acquired by repetition of Np.

In dynamic measurement, time series data is obtained by repeating such measurement for acquiring two- or three-dimensional data. One imaging time in such a dynamic measurement is the time obtained by multiplying the repetition time TR by the phase encode number in the case of the two-dimensional measurement and the time obtained by multiplying the repetition time TR by the phase encode number and the slice encode number in the case of the three-dimensional measurement. To improve spatial resolution, therefore, the phase encode number and the slice encode number are preferably large but when they are large, the imaging time gets elongated and time resolution drops. In other words, spatial resolution and time resolution basically have the trade-off relation.

Therefore, in the MRI apparatus according to the invention, the k space is further divided into a plurality of areas and the measurement data of the same area is used in common for a plurality of time phases to substantially shorten one imaging time. This is a known technology disclosed in JP-A-2002-177240, for example. More concretely, all the data of the k space are not measured by one imaging. Instead, the k space is divided into a low spatial-frequency area (high repetitive-frequency measurement area) inclusive of the origin and a plurality of high spatial-frequency areas (low repetitive-frequency measurement area) not containing the origin, and the measurement sequence is controlled for each measurement area so that the high repetitive-frequency measurement areas can be measured with higher frequency than the low repetitive-frequency measurement areas with the divided measurement area being the unit. The measurement data of the low repetitive-frequency measurement area is used in common among a plurality of time phases or is interpolated by using the measurement data of the same low repetitive-frequency measurement area measured in a different time phase to create the measurement data of the low repetitive-frequency measurement area of a desired time phase. Thus the one imaging time is substantially shortened.

The measurement data of each measurement area that is practically measured or is created by interpolation is stored in the magnetic disk 18, for example, and is read into and used by the CPU 8 for image reconstruction, etc, whenever necessary.

According to this technology, since the full number of slice encodes or phase encodes are not executed in each imaging, each imaging time can be shortened and time resolution of dynamic measurement can be improved. As for the center area (low spatial frequency area) of the k space that decides the contrast important for the diagnosis, the time change of the concentration of the contrast agent concentration can be reliably grasped because time resolution can be improved by high frequency measurement.

Figure 1A:
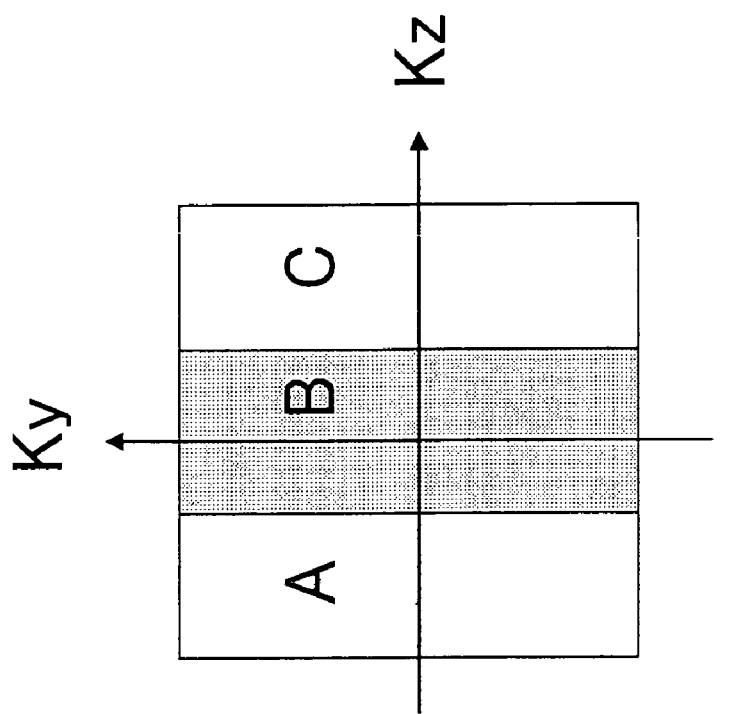
FIGS. 1a and 1b illustrate views showing division examples of a three-dimensional k space.
Figure 1B:
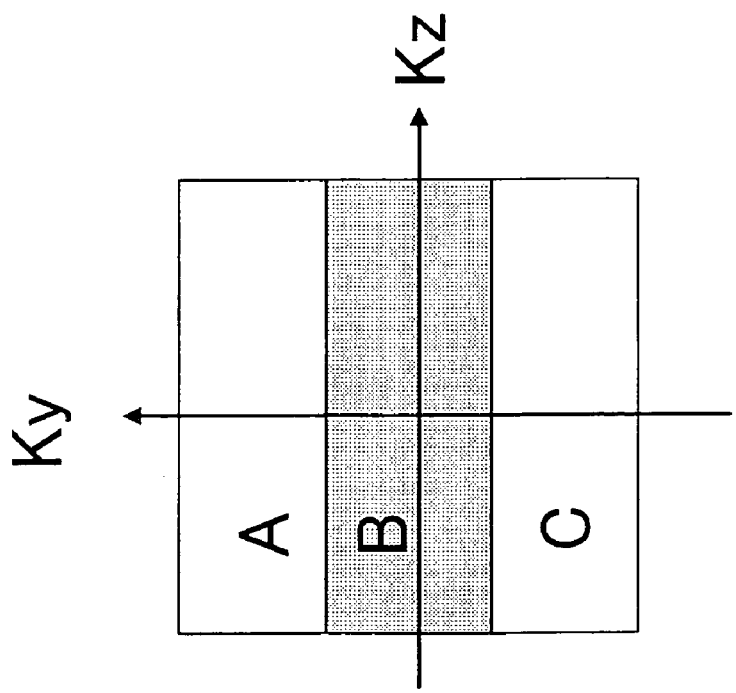

FIGS. 1a and 1b illustrate examples of the area division of the three-dimensional k space. FIG. 1a shows the case where the three-dimensional k space is divided into the low spatial-frequency area B (high frequency measurement area) inclusive of the origin and the other high spatial-frequency areas A and C (low repetitive-frequency measurement areas) A and C by a plane Kx-kz defined by the readout direction (Kx) and the slice encode direction (kz) in terms of the Kx=0 plane. Measurement is made with higher frequency for the high repetitive-frequency measurement area B than the low repetitive-frequency measurement areas A and C. However, division of the k space is not limited to this example. For example, division may be made by the plane Kx-Ky defined by the readout direction (Kx) and the phase encode direction (Ky). FIG. 1b shows the Kx=0 plane when division is made as described above. Alternatively, as described in JP-A-2002-177240, division may be made more finely. In short, division may well be made in such a manner as to divide into the area containing the origin as the high repetitive-frequency measurement area and the area not containing the origin as the low repetitive-frequency measurement area. Furthermore, each low repetitive-frequency measurement area may be divided further finely into at least two areas independently of each other.

FIRST EMBODIMENT

Next, the MRI apparatus according to the first embodiment of the invention will be explained. When the k space data of a plurality of time phases is measured by conducting dynamic measurement, the measurement sequence of each measurement area to be measured in time series is controlled (that is, arbitrarily changed) so that the measurement period of the high-repetitive frequency measurement area contains the artery phase (the time phase in which the artery is mainly depicted).

Figure 2:
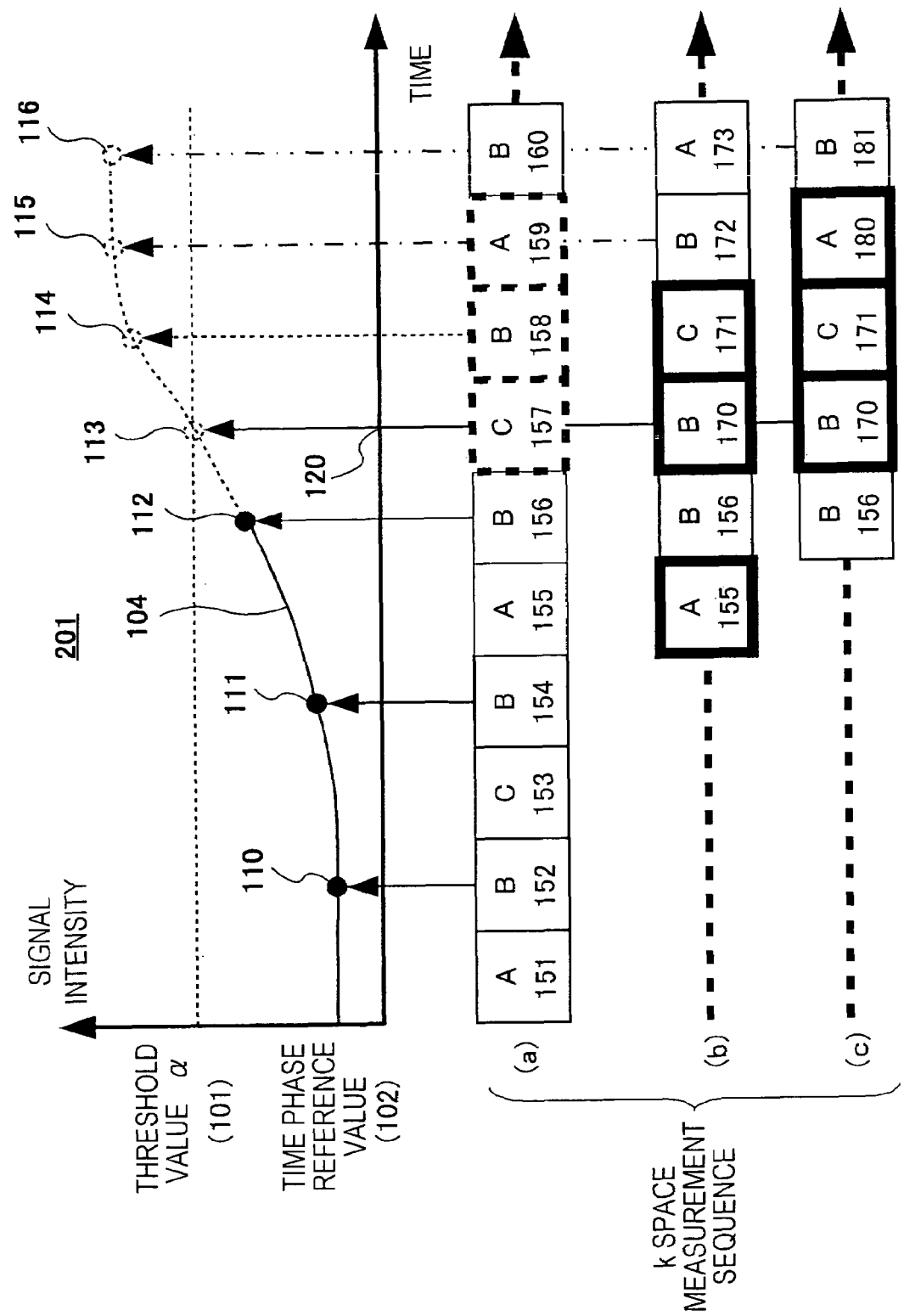
FIG. 2 is a view showing a graph of a time change by plotting time phase evaluation values by three-dimensional dynamic measurement and a display example of a measurement sequence of each measurement area divided.

FIG. 2 shows an example of the first embodiment. FIG. 2 shows the mode of the time change of the time phase evaluation value (102) by the three-dimensional dynamic measurement by using the MRI apparatus described already and an example of the measurement sequence of each measurement area divided.

Here, the term "time phase evaluation value" means an addition value after the k space origin data of the high frequency measurement area or uni-dimensional echo data in the readout direction (Kx) containing this origin data is subjected to uni-dimensional Fourier transform (1DFT) and both are arithmetically equivalent. Ideally, the k space origin data is the maximum value among the echo data measured, that is, the echo center value, but there is the case where the maximum position of the echo data and the k space origin somewhat deviate from each other due to influences of an eddy current, for example. In such a case, portions near the k space origin are retrieved to acquire the maximum value of the echo data and to use it as a substitution value of the echo center value. Alternatively, the echo center value is predicted and acquired by interpolation of this maximum value and the nearby echo data. The time phase evaluation value will mean the value obtained in this way unless otherwise stipulated specifically.

First, initial setting is made for dynamic measurement before the three-dimensional dynamic measurement is started. A known gradient echo system pulse sequence shown in FIG. 9 is used as the pulse sequence. The division of the k space is done in such a way, for example, the three-dimensional k space being divided by the plane Kx-kz defined by the readout direction (Kx) and the slice encode direction (kz) into the high repetitive-frequency measurement area B containing the origin and the low repetitive-frequency measurement areas A and C not containing the origin as shown in FIG. 1a.

After initial setting, the pulse sequence is activated and the dynamic measurement is started. The contrast agent is injected from an arbitrary timing into a predetermined blood vessel of the subject such as an elbow vein. The measurement sequence of each measurement area can be made regular such as A(151)→B(152)→C(153)→B(154)→A(155)→B(156)→C(157)→B(158)→A(159)→B(160)→ . . . as shown in (a) when the start timing 120 of the artery phase is not taken into consideration. In this case, the time phase evaluation values 110, 111, 112, 114, 116 . . . can be acquired. [C(157), B(158) and A(159)], for example, is selected as a set for image reconstruction by a later-appearing selection method of the measurement area inclusive of the artery phase and their k space data are extracted and used for image reconstruction. According to such a measurement sequence, the high repetitive-frequency measurement area B is measured at a frequency twice that of the low repetitive-frequency measurement areas A and C and each low repetitive-frequency measurement area is uniformly measured.

Incidentally, the reconstruction image may be displayed on the real time basis in synchronism with the progress of the dynamic measurement if the image reconstruction processing can be made in time.

Because the time phase evaluation value 112 of B(156) starts rising with respect to the time phase evaluation value 111 of B(154), however, the preceding time phase evaluation values 110 and 111 of B(152) and (B154) are calculated at the point at which the time phase evaluation value 112 is acquired and in this way, the timing 120 at which the value of the time phase evaluation value acquired from the high repetitive-frequency measurement area B thereafter measured reaches a threshold value α(101), that is, the start timing 120 of the artery phase, can be predicted. The measurement sequence of each measurement area after B(156) is controlled (that is, arbitrarily changed) so that this predicted timing 120 can be contained in the measurement period of the high repetitive-frequency measurement area B to be thereafter measured.

As shown in FIG. 2(b), for example, the measurement sequence is changed so that the high repetitive-frequency measurement area B(170) can be again measured in match with the start timing 120 of the artery phase immediately after the measurement of the high repetitive-frequency measurement area B(156). By taking into consideration the fact that the low repetitive-frequency measurement area A(155) exists immediately before B(156), the other low frequency measurement area C(171) is then measured. Subsequently, each measurement area B(172), A(173) . . . is serially measured in the same sequence pattern as (a). Therefore, the time phase evaluation values practically measured after the time phase evaluation value 112 are 113, 115 . . . and the time phase evaluation values 114 and 116 that should be originally measured are not measured in practice. Next, B(156) and C(171) that are time-wise closest to B(170) as the center, that is, [A(155), B(170), C(171)], are selected as the set for image reconstruction and the image at the start timing 120 of the artery phase is reconstructed by extracting their k space data.

Alternatively, as shown in FIG. 2(c), A(180) having the same time interval with respect to B(170) as A(155) is measured because B(170) and C(171) are measured in FIG. 2(b) after C(171), and each measurement area B(181) . . . is thereafter measured serially in the same pattern as FIG. 2(a). Therefore, the time phase evaluation values practically measured after the time evaluation value 112 are 113, 116 and so forth, and the time phase evaluation value 114 that should be originally measured is not measured in practice. Next, [B(170), C(171), A(180)] is selected as the set for image reconstruction, their k space data are extracted and the image at the start timing 120 of the artery phase is reconstructed.

Here, prediction of the timing 120 at which the value of the time phase evaluation value reaches the threshold value α(101) can be made by determining a signal intensity change curve (Time-Intensity-Curve) TIC104 approximately representing the time change of the measured time phase evaluation values by spline interpolation from the time phase evaluation values so far measured at this point of time, and determining the timing 120 reaching the threshold value α(101) by extrapolation.

In other words, the time phase evaluation value is acquired from the measurement data of the high repetitive-frequency measurement area measured, the signal intensity change curve 104 is updated by adding the time phase evaluation so acquired, the timing 120 is predicted on the basis of the signal intensity change curve 104 so updated and the subsequent measurement sequence of each measurement area is controlled based on that prediction so that the measurement period of the high repetitive-frequency measurement area to be later measured can contain the predicted timing 120. This prediction and control of the measurement sequence based on this prediction are repeated until the time phase evaluation value having the threshold value α(101) or greater can be acquired in practice.

The value of the threshold value α(101) is preferably 1.8 times or more of the base line value of the time phase evaluation values obtained before the value of the time phase evaluation value starts rising. In FIG. 2(a), for example, the time phase evaluation value 110 and the mean of the time phase evaluation values obtained before this value 110 are used as the base line value and the value of its 1.8 times is used as the threshold value α(101).

The process for prediction of the timing 120 and for setting the threshold value is stored as a program in the magnetic disk 18, for example, and is read into and executed by the CPU 8 with the necessary data similarly stored in the magnetic disk 18. The prediction value of the time 120 and the threshold value as the processing result are stored in the magnetic disk 18, for example, and used thereafter for the processing described above.

Figure 3A:
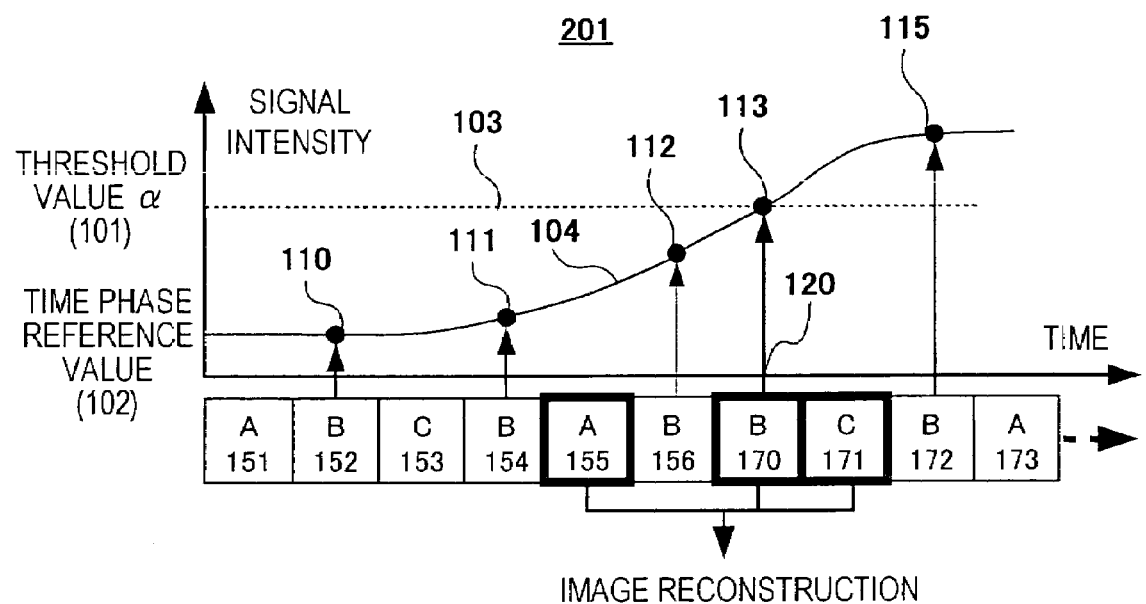
FIGS. 3a and 3b illustrate views showing an example where a measurement result and an image are displayed after dynamic measurement is made.
Figure 3B:
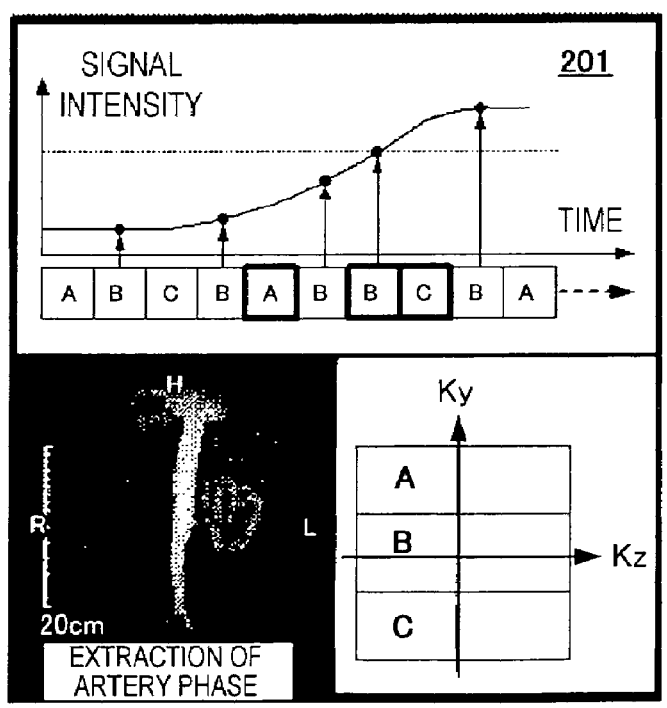

Next, decision of the artery phase after the dynamic measurement described above is finished will be explained with reference to FIG. 3a and 3b. FIGS. 3a and 3b show an example where the dynamic measurement is made under the same condition as in FIG. 2 and the measurement result and the image are displayed. FIG. 3a shows a graph 201 of a plot of the time phase evaluation value acquired in the measurement sequence of each measurement area shown in FIG. 2(b) and its signal intensity change curve 104, and the measurement sequence and the measurement period of each measurement area with the time axis being in common with that of the graph 201. Each measurement area is represented by a rectangle and the length in the time axis direction (horizontal direction) represents the measurement period. On the other hand, the length in the signal intensity direction (vertical direction) does not have specific meaning but is desirably a suitable length for easy viewing. FIG. 3b shows an example by combining the graph 201 shown in FIG. 3a, the projection image of the selected artery phase and the mode of area division of the k space on one screen and displaying them on the display 20 (FIG. 8), for example.

Among a plurality of time phases in the graph 201 shown in FIG. 3a, the time phase at the timing 120 at which the time phase evaluation value reaches the threshold value α(101) calculated during the dynamic measurement is regarded as the artery phase, and the high repetitive-frequency measurement area B(170) calculated in this time phase and the low repetitive-frequency measurement areas A(155) and C(171) close time-wise to this high repetitive-frequency measurement area B(170) and constituting other areas of the k space are selected. To explicitly represent the selection, the rectangles of the selected measurement areas are represented by thick frames as shown in 3a and 3b, for example.

Incidentally, when the high repetitive-frequency measurement area containing the time phase of the timing 120 reaching the threshold value α(101) does not exist, the threshold value α(101) or the time 120 is changed or designated on the graph 201 to be explained next. Alternatively, the high repetitive-frequency measurement area closest to the timing 120 reaching the threshold value α(101) is selected as will be explained in detail in the later-appearing second embodiment. In this way, the optimum high repetitive-frequency measurement area and the low repetitive-frequency measurement areas close time-wise to the former can be selected.

The k space data of the image reconstruction set [A(155), B(170),C(171)] of the selected measurement area is extracted from the measurement data stored in the magnetic disk 18, for example, and is subjected to Fourier transform to acquire the three-dimensional image data and a projection processing is further executed, so that the two-dimensional projection blood vessel image of the intended artery phase is displayed after imaging on the display 20 as shown at the lower left of FIG. 3b. In the image of the artery phase, the artery is depicted to high signals as a whole by the contrast agent.

Here, the projection processing can be executed by employing a known projection method such as MIP (Maximum Intensity Projection) processing that regards the maximum signal value on a projection axis as the blood vessel, for example. The image reconstruction processing is stored as a program in the magnetic disk 18, for example, and is read into and executed by the CPU 8 with the k space data necessary for the image reconstruction and stored similarly in the magnetic disk 18. The reconstruction image as the execution result is preserved in the magnetic disk 18, for example.

Incidentally, the lower right of FIG. 3b shows the mode of division of the k space employed in this dynamic measurement. This is the same as FIG. 1a.

When the blood vessel image displayed is not satisfactory, the adaptable measurement area can be selected by directly changing the threshold value α(101) on the display 20 or by directly designating the start timing 120 of the artery phase. Alternatively, the image reconstruction set of the measurement area can be directly designated. The k space data of the selected measurement area is extracted and the blood vessel image is reconstructed and displayed.

For example, when the threshold value α(101) is directly changed on the graph 201 displayed on the display 20, dotted line 103 representing the threshold value α(101) is directly moved up and down to a desired position by the track ball or mouse 23 so that the threshold value α(101) can be changed. Alternatively, the threshold value α(101) can be inputted and set by the keyboard 24. The time at the point of intersection between the threshold value (101) so changed and the signal intensity change curve 104 is regarded as the start timing 120 of the artery phase, and the high repetitive-frequency measurement area B closest to the timing 120 and the low repetitive-frequency measurement areas A and C close time-wise to the high repetitive-frequency measurement area B and constituting the other areas of the k space are selected. Their k space data is extracted to reconstruct the image and the resulting projection blood vessel image is displayed on the display 20. The change of the threshold value α(101) and reconstruction and display of the blood vessel image based on the former are repeated until the displayed blood vessel image proves satisfactory.

A concrete example will be explained with reference to FIG. 3a. When the dotted line 103 representing the threshold value α(101) is moved up to the position of the time phase evaluation value 115 by means of the track ball or mouse 23, for example, the start timing 120 of the artery phase becomes the same as the timing at which the time phase evaluation value 115 is acquired. Therefore, the high repetitive-frequency measurement area B(172) containing this time phase and the low repetitive-frequency measurement areas C(171) and A(173) close time-wise to this area B(172) are selected as the image reconstruction set.

Alternatively, when the start timing 120 of the artery phase is directly designated on the graph 201 displayed on the display 20, the desired point is designated by the track ball or mouse 23 on the time axis of the graph 201 or the signal intensity change curve 104 and the time corresponding to the designation point can be used as the timing 120 of the artery phase. The high repetitive-frequency measurement area B closest to the designated timing 120 and the low repetitive-frequency measurement areas A and C close time-wise to the high repetitive-frequency measurement area B and constituting other areas of the k space are selected. Each processing after this timing designation till the image display is the same as the case where the threshold value α(101) described above is changed. When the timing 120 for the artery phase is directly designated, too, designation of the timing 120 and the reconstruction and display of the blood vessel image based on the designation can be repeated until the displayed blood vessel image proves satisfactory.

This concrete example will be explained with reference to FIG. 3a. When a portion near the time phase evaluation value 112 is designated as the timing 120 of the artery phase by the track ball or mouse 23, for example, the high repetitive-frequency measurement area closest to the designated timing 120 is B(156), and A(155) and C(171) are selected as the image reconstruction set as the low repetitive-frequency measurement areas close time-wise to B(156).

Alternatively, the set of the measurement areas for direct image construction can be designated by selecting the rectangle of each measurement area displayed on the display 20 by the track ball or mouse 23. Each processing from this selection till image display is the same as the case where the threshold value α(101) described above is changed.

This concrete example will be explained with reference to FIG. 3a. The rectangle of [A(155), B(170), C(171)], for example, is selected as the image reconstruction set by the track ball or mouse 23. When a plurality of measurement areas of the same type are selected, the mean of their k space data can be used as the k space data of the measurement areas.

Incidentally, in the explanation of the embodiment given above, the high repetitive-frequency measurement area containing the start timing 120 of the artery phase within its measurement period and a plurality of low repetitive-frequency measurement areas filling the whole k space are used as the set of the measurement areas selected for image reconstruction. Though this is the best image reconstruction set, a minimum set for image construction can be constituted by the high repetitive-frequency measurement area containing the start timing 120 of the artery phase and at least one low frequency measurement area.

The low repetitive-frequency measurement areas are distributed time-wise symmetrically with the high repetitive-frequency measurement area containing the start timing 120 of the artery phase as the center and are closest to the high repetitive-frequency measurement area, that is, the low repetitive-frequency measurement areas are preferably measured immediately before or after the high frequency measurement area or time-wise continuously with the high repetitive-frequency measurement area. The second best selection is that at least one low repetitive-frequency measurement area is preferably measured immediately before or after the high repetitive-frequency measurement area. In an unavoidable case, the measurement periods of the high and low repetitive-frequency measurement areas selected as the image reconstruction set need not be time-wise continuous.

Figure 4:
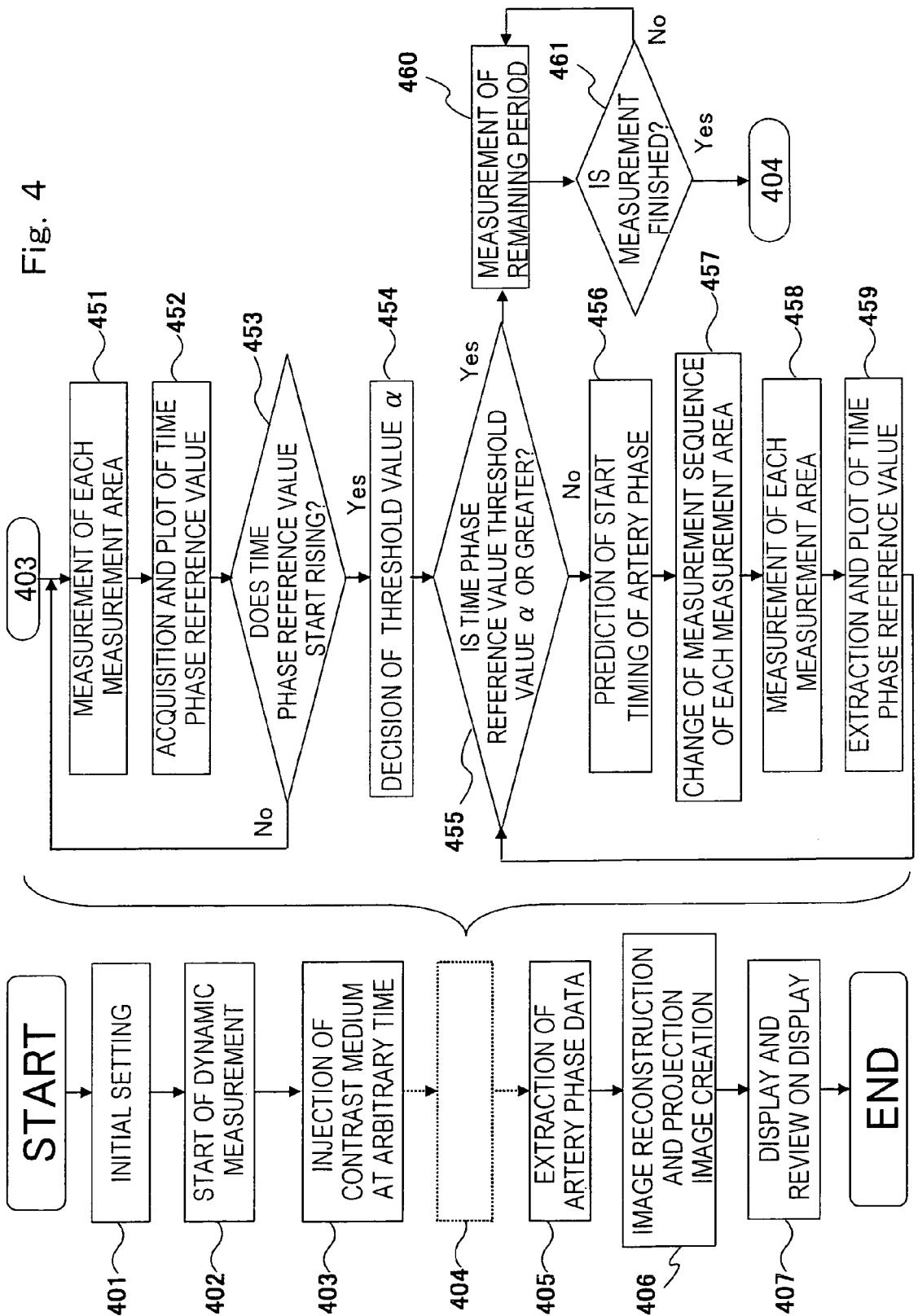
FIG. 4 is a view showing a processing flow of a first embodiment.

The processing flow of the first embodiment given above can be summarized and expressed as shown in FIG. 4. The processing of each step will be hereinafter explained in detail. A description will be first given to a flow as a whole shown on the left side of FIG. 4.

In Step 401, initial setting is made. For example, division of the k space and the measurement sequence of each measurement area divided are set. Division of the three-dimensional k space is made into three areas, that is, the high repetitive-frequency measurement area B containing the origin and the low repetitive-frequency measurement areas A and C not containing the origin, by the plane Kx-kz defined by the read direction (Kx) and the slice encode direction (kz) as shown in FIG. 1a, for example. Initial setting of the measurement sequence of each measurement area may be a predetermined sequence as shown in FIG. 2(a), for example.

In Step 402, the pulse sequence is activated and the dynamic measurement is started. The pulse sequence is a gradient echo system pulse sequence shown in FIG. 9, for example.

In Step 403, the contrast agent is injected at an arbitrary timing into the subject and contrast agent MRA is executed.

In Step 404, steps 451 to 461 as the entity of the dynamic measurement are executed. The detail of the steps will be described later.

In Step 405, the artery phase data (k space data) for the image reconstruction is extracted on the basis of the threshold value $\alpha(101)$ calculated and set in Step 404 after the dynamic measurement of Step 404 is completed. The detail will be explained in the later-appearing second embodiment and in Step 706.

In Step 406, Fourier transform is made for the k space data extracted in Step 405 to conduct image reconstruction. In the case of the three-dimensional reconstruction image, projection (MIP processing, for example) is further made in a desired direction to acquire a two-dimensional projection image.

In Step 407, the image acquired in Step 406 is displayed on the display 20, for example, and the image is read.

Next, the detailed flow of the dynamic measurement in Step 404 displayed on the right side of FIG. 4 will be explained.

In Step 451, each measurement area set in Step 401 is serially measured in the measurement sequence initially set in Step 401.

In Step 452, acquisition of the time phase evaluation value and plotting of this value on the graph 201 are made in synchronism with the progress of the dynamic measurement. In other words, the time evaluation value is acquired from each high frequency measurement area measured during the dynamic measurement and is plotted on the graph 201. Further, it is possible to display in superposition the signal intensity change curve 104 approximately expressing the time change by connecting the plot points.

In Step 453, whether or not the time phase evaluation value starts rising is checked. When the time phase evaluation value does not start rising, the flow returns to Step 451 and the measurement of each measurement area is continued in the measurement sequence initially set in Step 401. The flow shifts to Step 454 when the time phase evaluation value starts rising.

In Step 454, the threshold value $\alpha(101)$ is set by conducting calculation from the time phase evaluation value acquired before the start of rising. The threshold value $\alpha(101)$ can be set to 1.8 times the base line value of the time phase evaluation value as described already.

In Step 455, whether or not the time phase evaluation value is the threshold value $\alpha(101)$ or more is checked. When it is the threshold value $\alpha(101)$ or more, the flow proceeds to Step 460 and when it is less than the threshold value $\alpha(101)$ the flow proceeds to Step 456.

In Step 456, the start timing 120 of the artery phase is predicted from the time phase evaluation value acquired. The prediction method is as described already.

In Step 457, the measurement sequence of each measurement area is changed on the basis of the timing 120 predicted in Step 456 so that the measurement period of the high repetitive-frequency measurement area measured thereafter contains the timing 120. The mode of this change and control is as described already.

In Step 458, each measurement area is serially measured in accordance with the measurement sequence changed in Step 457.

In Step 459, acquisition of the time phase evaluation values and plotting of these values on the graph 201 are executed in the same way as in Step 452. The flow thereafter returns to Step 455.

In Step 460, each measurement area is continuously measured in the measurement sequence initially set in Step 401 or changed in Step 457 until the remaining dynamic measurement is finished after the acquired time phase evaluation value is the threshold value $\alpha(101)$ or more.

In Step 461, the end of the dynamic measurement is judged. The end judgment can be decided by the operator, or when the time phase evaluation value falls the half value of the peak value or less, for example. After the measurement is completed, the flow proceeds to Step 405. The flow returns to Step 460 when the measurement is not finished.

SECOND EMBODIMENT

Next, the MRI apparatus according to the second embodiment of the invention will be explained. This embodiment selects the high frequency measurement area closest to a desired artery phase and the low repetitive-frequency measurement areas close time-wise to the high frequency measurement area and constituting other areas of the k space after the dynamic measurement is executed to measure the k space data of a plurality of time phases. In other words, this is the form that does not predict the start timing of the artery phase while acquiring the time phase evaluation values in the first embodiment described above but serially measures each measurement area in a predetermined measurement sequence, detects a desired artery phase after the end of the dynamic measurement and acquires the image.

Figure 5A:
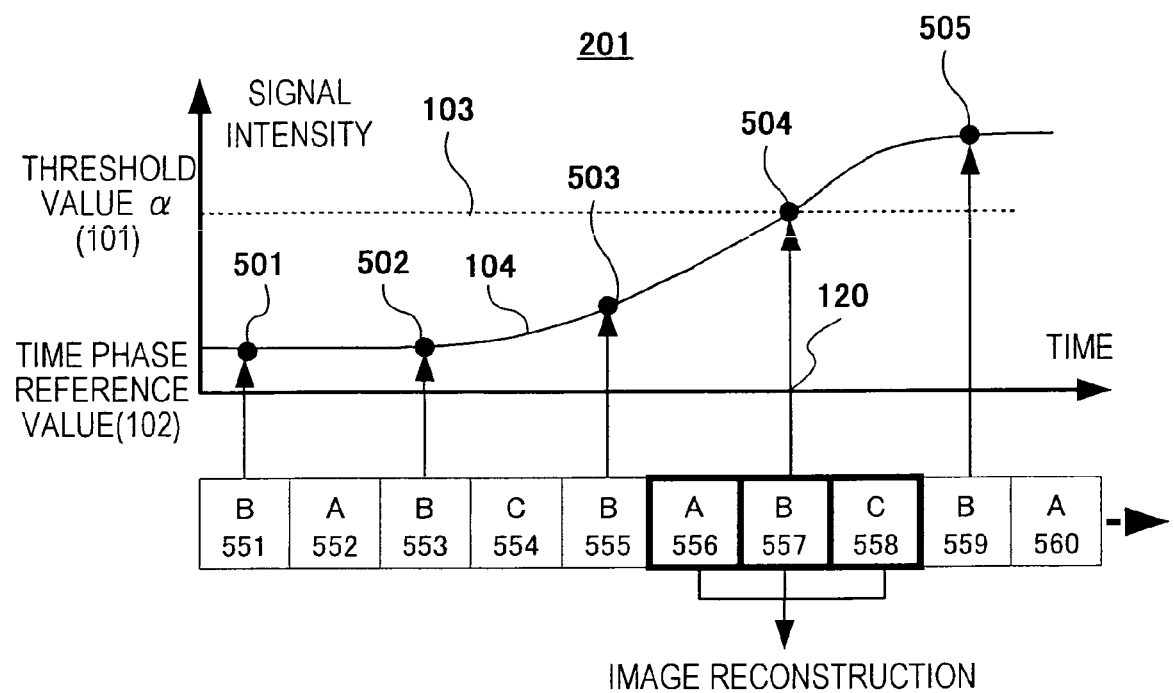
FIGS. 5a and 5b illustrate views showing a mode of time change of the time phase evaluation values measured and an example of a measurement sequence of each divided measurement area after dynamic measurement.
Figure 5B:
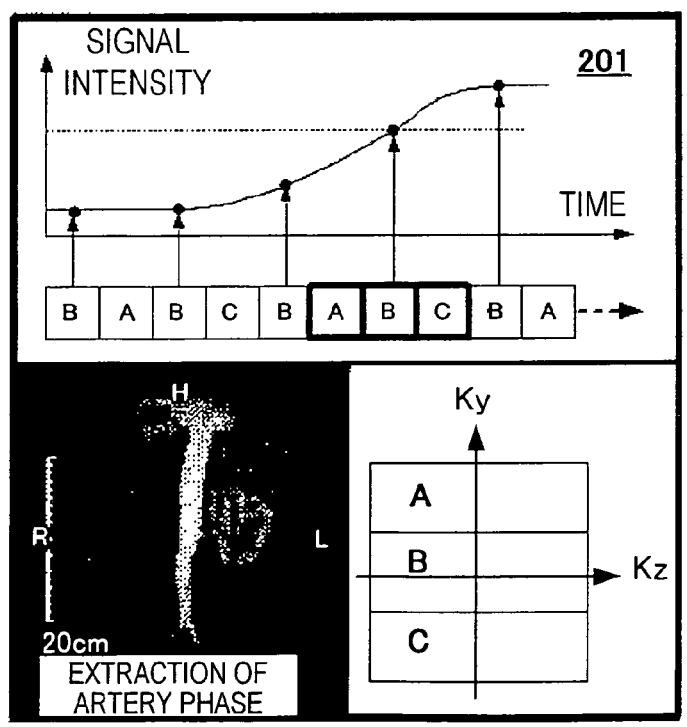

FIGS. 5a and 5b shows an example of this embodiment. FIGS. 5a and 5b show an example of the mode of the time change of the time phase evaluation values measured and the measurement sequence of each divided measurement area after the three-dimensional dynamic measurement by using the MRI apparatus described above is made in the same way as in FIGS. 2 and 3a-3b.

FIG. 5a shows the plot of the time phase evaluation values acquired from the high repetitive-frequency measurement area measured by measuring each measurement area in a predetermined measurement sequence in the dynamic measurement by the area division of the k space in the same way as in FIG. 1a, the graph 102 of the signal intensity change curve 104 and the display example of the measurement sequence and measurement period of each measurement area by using the time axis in common with the graph 102. The meaning of the rectangle of each measurement area is the same as in FIGS. 2 and 3a-3b.

FIG. 5b shows an example where the graph of FIG. 5a, the two-dimensional projection image of the selected artery phase and the mode of the area division of the k space are combined with one another on one screen and are displayed on the display 20, for example.

The measurement data of each measurement area measured here is stored in the magnetic disk 18, for example, and is thereafter read into and used by the CPU 8 at the time of the subsequent image reconstruction processing, etc, in the same way as in the first embodiment described above.

The pulse sequence is activated and the dynamic measurement is started in the same way as in FIG. 2. The contrast medium is injected at an arbitrary timing to a predetermined blood vessel of the subject such as an elbow vein and the three-dimensional dynamic measurement is started. A known gradient echo pulse sequence such as the one shown in FIG. 9 is used for the pulse sequence. The k space is divided into three areas, that is, the high repetitive-frequency measurement area B containing the origin and the low repetitive-frequency measurement areas A and C not containing the origin by the plane Kx-kz defined by the read direction (Kx) and the slice encode direction (Kz) as shown in FIG. 1a, for example. In this embodiment, however, each measurement area is measured in a predetermined sequence until the dynamic measurement is completed. The measurement sequence of each area can be set to B(551)→A(552)→B(553) →C(554)→B(555)→A(556)→B(557)→C(558)→B(559) →A(560) . . . for example. In this case, the time phase evaluation values 501, 502, 503, 504, 505, and so forth, can be acquired. In this measurement sequence, the high repetitive-frequency measurement area B is measured twice as often as the low repetitive-frequency measurement areas A and C and each low repetitive-frequency measurement area A, C is uniformly measured in the same way as in FIG. 2(a).

Whenever the high repetitive-frequency measurement area is measured, its time phase valuation value is acquired and is plotted on the graph 201. These time phase evaluation values are connected to one another and the signal intensity change curve 104 approximately representing their time change is displayed in superposition.

The time phase of the timing 120 at which the time phase evaluation value reaches the threshold value α(101) is determined after the dynamic measurement is completed. For example, the time phase evaluation values are acquired from the measurement data of a plurality of high repetitive-frequency measurement areas stored in the magnetic disk 18, for example, and the time change of each time phase evaluation value is traced so that the time phase of the timing 120 at which the time phase evaluation value reaches the threshold value α(101) is determined.

In FIG. 5a, the time phase of the timing at which the time phase evaluation value reaches the threshold value α(101) is in agreement with the time phase of the time phase evaluation value 504 acquired from the high frequency measurement area B(557). Therefore, this high repetitive-frequency measurement area B(557) and the low repetitive-frequency measurement areas A(556) and C(558) close time-wise to this high repetitive-frequency measurement area B(557) and constituting other areas of the k space are selected and [A(556), B(557), C(558)] is regarded as the image reconstruction set. The k space data is extracted and image reconstruction is made to display the two-dimensional projection image.)

The explanation of FIG. 5a given above deals with the case where the measurement period of the high repetitive-frequency measurement area B contains the start timing 120 of the artery phase but in many cases, the start timing 120 deviates. In such a case, the high repetitive-frequency measurement area that exists before or after the start timing 120 of the artery phase and is time-wise closest to the timing 120 and the low repetitive-frequency measurement areas close time-wise to the high repetitive-frequency measurement area and constituting other areas of the k space are selected as the image reconstruction set. The image reconstruction set of a desired measurement area is suitably selected after the start timing 120 of the artery phase but it may be selected immediately before the timing 120. This will be explained with reference to FIG. 6.

Figure 6:
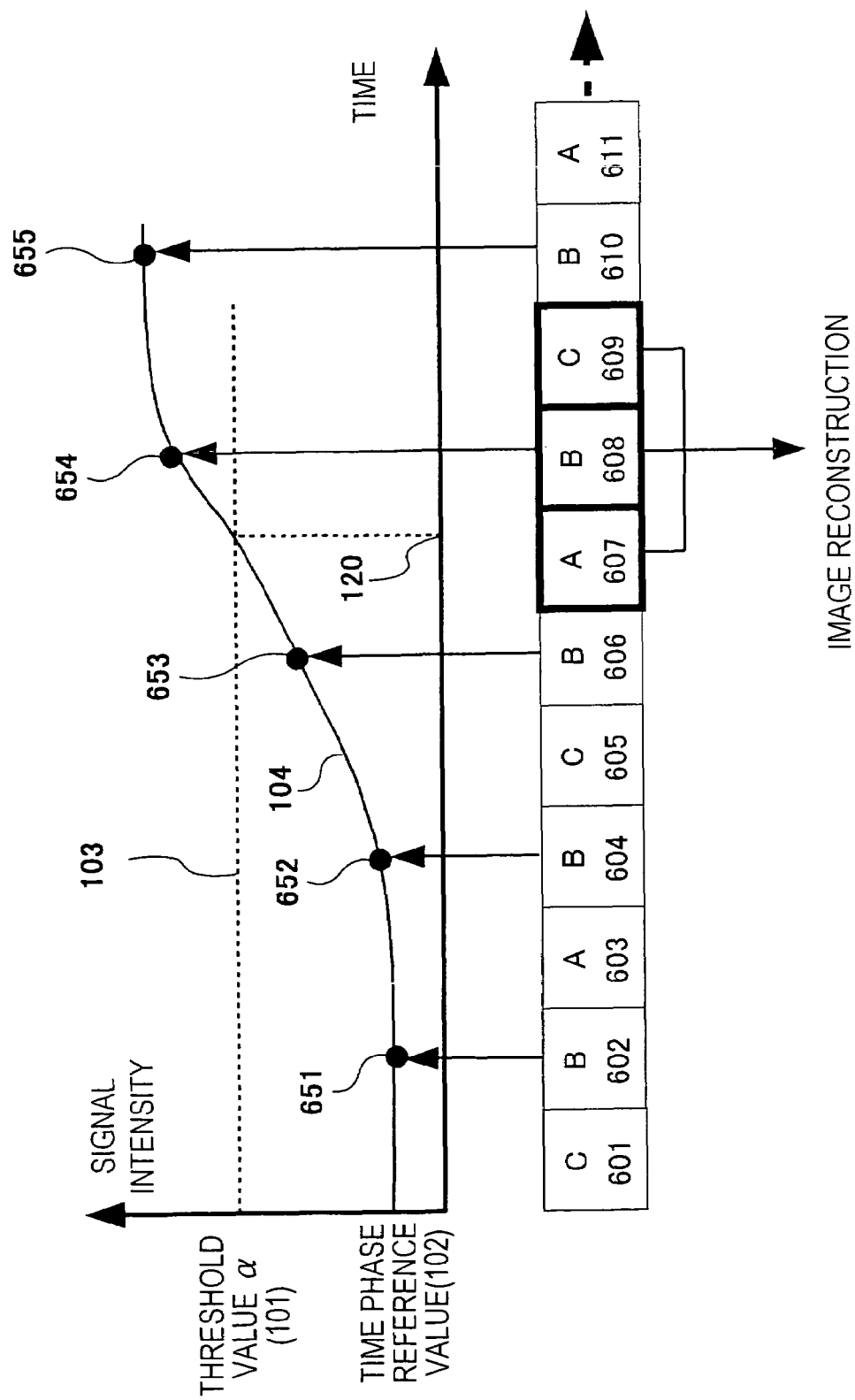
FIG. 6 is a view showing the case where a measurement period of the high frequency measurement area deviates from a start timing of the artery phase.

In FIG. 6, since the area measured in the time phase containing the start timing 120 of the artery phase is A(607) the time phase value 654 acquired from the high repetitive-frequency measurement area B(608) measured after the area A(607) exceeds the threshold value α(101) for the first time. Therefore, [A(607), B(608), C(609)] is selected as the image reconstruction set. Alternatively, when the time phase of the time phase evaluation value 653 immediately before the start timing 120 of the artery phase is selected, [C(605), B(606), A(607)] can be selected as the image reconstruction set with the high repetitive-frequency measurement area B (606), from which the time phase evaluation value is acquired, as the center. The k space data of each of the selected measurement areas is extracted from the measurement data stored in the magnetic disk 18, for example, image reconstruction is made and the two-dimensional projection image is displayed.

In the second embodiment, too, as in the first embodiment the threshold value α(101) or the start timing 120 of the artery phase is directly changed or designated on the graph 201 after the dynamic measurement is completed and the measurement areas can be selected in accordance with the change or designation. Alternatively, the set of the measurement areas for image reconstruction can be selected from the rectangles of the measurement areas displayed on the display 20 by using the track ball or mouse 23, for example.

Figure 7:
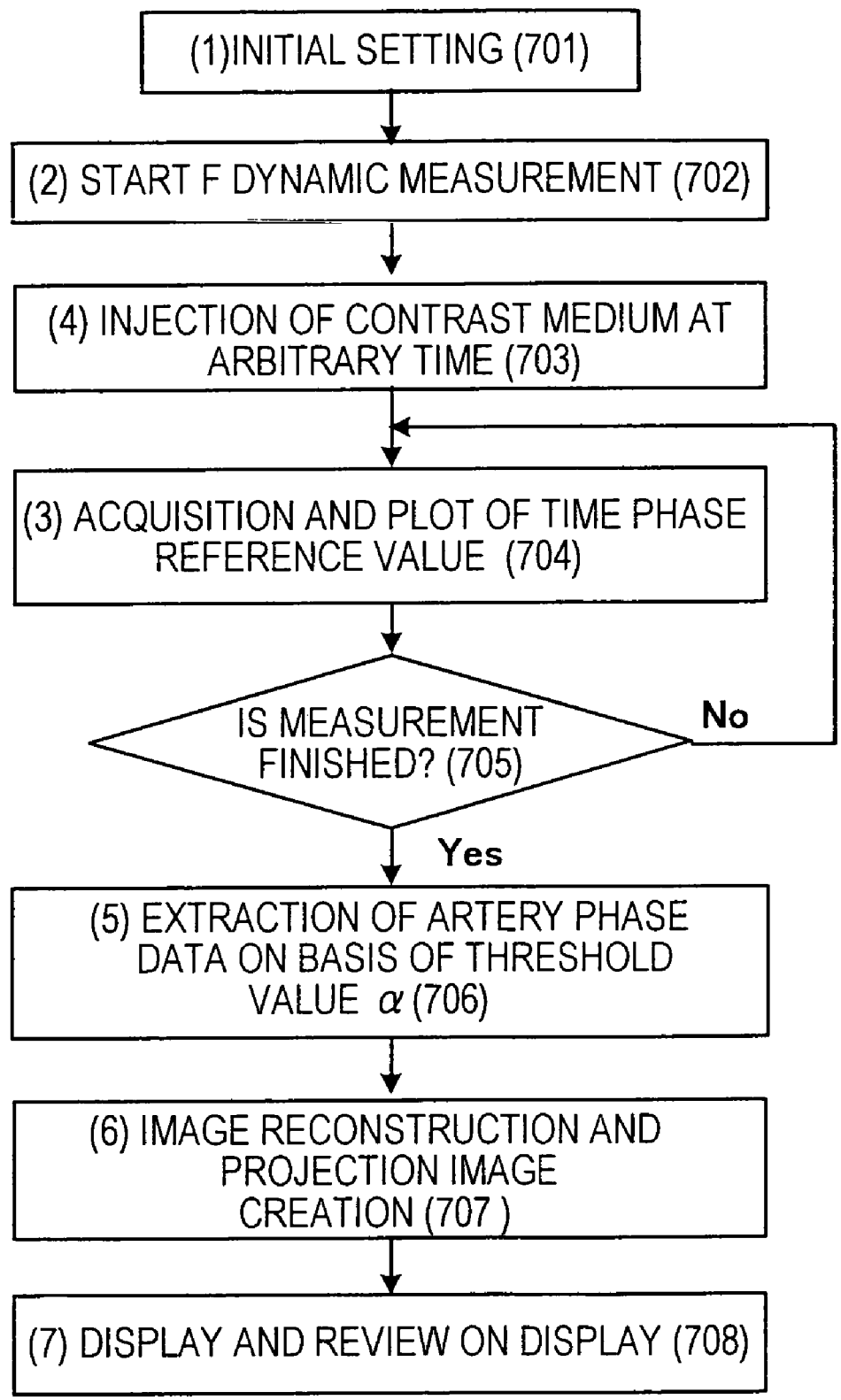
FIG. 7 is a view showing a processing flow of a second embodiment.

The processing flow of the second embodiment can be expressed as in FIG. 7. The processing of each step will be hereinafter explained in detail.

In Step 701, initial setting is made. For example, division of the k space and setting of the measurement sequence of each divided measurement area and setting of the threshold value α(101) are made. In the case of the three-dimensional k space, division is made as shown in FIG. 1a, for example. In initial setting of the measurement sequence of each measurement area, the predetermined sequence shown in FIG. 5a can be set as initial setting. Setting of the threshold value α(101) can be made by directly moving up and down the dotted line 103 representing the threshold value α(101) to a desired position on the signal intensity axis of the graph 201 by using the track ball or mouse 23. Alternatively, the threshold value α(101) can be directly input and set from the keyboard 24.

In Step 702, the dynamic measurement is started by activating the pulse sequence in the same way as in Step 402. The pulse sequence is the gradient echo system pulse sequence shown in FIG. 9, for example.

In Step 703, the contract agent is injected at an arbitrary timing to the subject after the start of the dynamic measurement and contract agent MRA is carried out.

In Step 704, the time phase evaluation value is acquired from each high frequency measurement area in synchronism with the progress of the dynamic measurement and is plotted on the graph 201. The plots are then connected to one another and the signal intensity change curve 104 approximately representing their time change may be displayed in superposition.

In Step 705, it is judged the dynamic measurement is finished. The end judgment can be made when the time phase evaluation value falls the half value or less of the peak value or by the judgment of the operator. After the end of the measurement, the flow proceeds to Step 706 or returns to Step 704 when the measurement is not finished.

In Step 706, the artery phase data (k space data) for image reconstruction is extracted on the basis of the threshold value α(101). In other words, the high repetitive-frequency measurement area closest time-wise to the timing 120 and the low repetitive-frequency measurement areas close time-wise to the high repetitive-frequency measurement area and constituting other areas of the k space are selected as the image reconstruction set before or after the timing 120 at which the time phase evaluation value reaches the threshold value α(101) or greater.

In Step 707, image reconstruction is made in the same way as in Step 406 described already.

In Step 708, image obtained in Step 707 is displayed on the display and is trace-read.

The above mainly explains each embodiment of the invention about the case where the three-dimensional image is extracted as the artery phase but the invention is not particularly limited to these embodiments and can be applied to extraction other than the artery phase. For example, the invention can be applied to depiction of the vein phase for depicting the vein in high luminance. The invention can be applied to not only three-dimensional measurement but also acquisition of the two-dimensional image by two-dimensional dynamic measurement. In the case of the two-dimensional measurement, however, slice encode is not executed.

According to the invention explained above, it is possible to easily and instantaneously acquire the start timing of the desired time phase by serially extracting the time phase evaluation values from the time series data measured by the dynamic measurement and tracing the time change and to reconstruct and display the image containing the time phase. Consequently, in MRA using the contrast agent, the k space data of the intended artery phase can be extracted easily and instantaneously from a large number of time series measurement data containing a plurality of time phases and the image can be displayed.

The invention claimed is:

1. A magnetic resonance imaging apparatus including:

measurement control means for dividing a k space into a high repetitive-frequency measurement area containing an origin of the k space and measured at a high repetitive-frequency and a plurality of low repetitive-frequency measurement areas not containing the origin and measured at a low repetitive-frequency, and obtaining k space data by repeating measurement of said high repetitive-frequency measurement area and measurement of at least one of said low repetitive-frequency measurement areas between said measurements of the high repetitive-frequency measurement area in a predetermined measurement order;

signal processing means for reconstructing an image by using all or a portion of the k space data as an image reconstruction set; and display means for displaying the resulting image;

wherein said signal processing means acquires a time phase evaluation value from said high repetitive-frequency measurement area, determines a time phase at which said time phase evaluation value reaches a predetermined threshold value or greater, and said measurement control means rearranges the predetermined measurement order of some of said high repetitive-frequency measurement area and said at least one of said low repetitive-frequency measurement areas in such a manner that a measurement period of said high repetitive-frequency measurement area contains said time phase.

2. A magnetic resonance imaging apparatus according to claim 1, wherein at least one low repetitive-frequency measurement area constituting said image reconstruction set is a measurement area measured immediately before or immediately after said high repetitive-frequency measurement area constituting said image reconstruction set.

3. A magnetic resonance imaging apparatus according to claim 1, wherein selection of each of said measurement areas constituting said image reconstruction set is made in such a manner as to contain the whole area of the k space.

4. A magnetic resonance imaging apparatus according to claim 1, wherein said signal processing means predicts a timing of said time phase from a time change of said time phase evaluation value, and said measurement control means controls the measurement order of each of said high repetitive-frequency measurement areas on the basis of the timing predicted.

5. A magnetic resonance imaging apparatus according to claim 1, wherein said time phase evaluation value is a substantial peak value of the k space data in said high repetitive-frequency measurement area.

6. A magnetic resonance imaging apparatus according to claim 5, wherein said threshold value is at least 1.8 times a base line value of said time phase evaluation value.

7. A magnetic resonance imaging apparatus according to claim 5 wherein said threshold value is at least 80% of a maximum value of said time phase evaluation value.

8. A magnetic resonance imaging apparatus according to claim 1, wherein said time phase evaluation value is an addition value of data obtained after one-dimensional data in a read direction containing the origin of the k space in said high repetitive-frequency measurement area is subjected to Fourier transform.

9. A magnetic resonance imaging apparatus according to claim 1, wherein said signal processing means repeats acquisition a plurality of times to obtain a plurality of time phase evaluation values, and said display means displays in a time series the plurality of time phase evaluation values.

10. A magnetic resonance imaging apparatus according to claim 9, wherein said display means displays a signal intensity change curve approximately representing time changes by connecting the plurality of time phase evaluation values displayed in the time series.

11. A magnetic resonance imaging apparatus according to claim 9, wherein said display means has means for setting said threshold value.

12. A magnetic resonance imaging apparatus according to claim 9, wherein said display means displays a measurement order of each of said measurement areas and its measurement time by using the same time axis as the display of said time phase evaluation value.

13. A magnetic resonance imaging apparatus according to claim 1, wherein said k space data is data on which concentration information of a contrast medium injected to a subject is reflected, said image contains a blood vessel image of said subject and said time phase is a time phase in which an artery of the subject is emphasized by said contrast agent.

14. A magnetic resonance imaging apparatus according to claim 1 wherein said k space is a three-dimensional space that comprises a slice encode direction, a phase encode direction and a readout direction, and division of said k space is division by a plane parallel to said readout direction.

15. A magnetic resonance imaging apparatus according to claim 14, wherein said signal processing means executes a projection processing on a two-dimensional plane after three-dimensional reconstruction.

16. A magnetic resonance imaging method comprising:
a division step of dividing a k space into a high repetitive-frequency measurement area containing an origin of said k space and measured at a high repetitive-frequency and a plurality of low repetitive-frequency measurement areas not containing said origin and measured at a low repetitive-frequency;
a measurement control step of repeating measurement of said high repetitive-frequency measurement area and measurement of at least one of said low repetitive-frequency measurement areas between said measurements of the high repetitive-frequency measurement area in a predetermined measurement order of said high repetitive-frequency measurement area;
a step of conducting image reconstruction by using said k space data; and
a step of displaying the resulting image;
wherein said measurement control step includes a step of acquiring a time phase evaluation value from said high repetitive-frequency measurement area, a step of determining a time phase in which said time phase evaluation value is a predetermined threshold value or greater, and
said measurement control step rearranges the predetermined measurement order of some of said measurement areas in such a manner that a measurement period of said high repetitive-frequency measurement area contains said time phase.

17. A magnetic resonance imaging apparatus including:
measurement control means for dividing a k space into a high repetitive-frequency measurement area containing an origin of the k space and measured at a high repetitive-frequency and a plurality of low repetitive-frequency measurement areas not containing the origin and measured at a low repetitive-frequency, and obtaining k space data by repeating measurement of said high repetitive-frequency measurement area and measurement of each of said low repetitive-frequency measurement areas between said measurements of the high repetitive-frequency measurement area;
signal processing means for reconstructing an image by using all or a portion of the k space data as an image reconstruction set; and
display means for displaying the resulting image; wherein
said measurement control means rearranges an order of the high repetitive-frequency measurement area from a predetermined measurement order in such a manner that a measurement period of said high repetitive-frequency measurement area contains a desired time phase, as said image reconstruction set has been inserted as a separate paragraph,
said signal processing means selects the high repetitive-frequency measurement area containing, or being time-wise close to, the desired time phase and at least one low repetitive-frequency measurement area measured time-wise close to said high repetitive-frequency measurement area, from the measured measurement areas, and executes image reconstruction by using the k space data of said image reconstruction set.

18. The magnetic resonance imaging apparatus of claim 17, wherein said signal processing means acquires a time phase evaluation value from said high repetitive-frequency measurement area, determines said desired time phase at which said time phase evaluation value reaches a designated threshold value or greater.

19. A magnetic resonance imaging apparatus according to claim 18, wherein said signal processing means determines said time phase after repetition of said measurements of said high repetitive-frequency measurement area.

20. A magnetic resonance imaging apparatus according to claim 18, wherein said display means has means for designating said time phase, and said signal processing means selects said high repetitive-frequency measurement area closest to said time phase designated.

21. A magnetic resonance imaging apparatus according to claim 18, wherein said display means has means for selecting each of said measurement areas constituting said image reconstruction set.

22. A magnetic resonance imaging apparatus according to claim 18, wherein said display means differs display aspect of each of said selected measurement areas from display aspect of other measurement areas not selected.

* * * * *